(12) United States Patent
Dobelle

(10) Patent No.: US 6,658,299 B1
(45) Date of Patent: Dec. 2, 2003

(54) ARTIFICIAL SYSTEM FOR VISION AND THE LIKE

(76) Inventor: William H. Dobelle, 4 Clamshell La., Asharoken, NY (US) 11768-1141

( * ) Notice: Subject to any disclaimer, the term of this patent is extended or adjusted under 35 U.S.C. 154(b) by 0 days.

(21) Appl. No.: 09/477,554

(22) Filed: Jan. 4, 2000

(51) Int. Cl.[7] .................................................. A61N 1/08
(52) U.S. Cl. ...................................................... 607/54
(58) Field of Search ..................... 607/54, 53; 600/558; 382/266

(56) References Cited

U.S. PATENT DOCUMENTS

| | | |
|---|---|---|
| 2,721,316 A | 10/1955 | Shaw |
| 3,320,947 A | 5/1967 | Knoll |
| 3,449,768 A | 6/1969 | Doyle |
| 3,594,823 A | 7/1971 | Collins |
| 3,628,193 A | 12/1971 | Collins |
| 3,699,970 A | 10/1972 | Brindley |
| 3,848,608 A | 11/1974 | Leonard |
| 4,254,776 A | 3/1981 | Tanie |
| 4,551,149 A | 11/1985 | Sciarra |
| 4,611,596 A | 9/1986 | Wasserman |
| 4,664,117 A | 5/1987 | Beck |
| 4,793,353 A | 12/1988 | Borkan |
| 4,837,049 A | 6/1989 | Byers |
| 4,979,508 A | 12/1990 | Beck |
| 5,037,376 A | 8/1991 | Richmond |
| 5,159,927 A | 11/1992 | Schmid |
| 5,411,540 A | 5/1995 | Edell |
| 5,563,713 A | * 10/1996 | Sugiura ...................... 382/256 |
| 5,674,263 A | 10/1997 | Yamamoto |
| 5,878,154 A | 3/1999 | Schimmelpfennig |
| 5,978,507 A | * 11/1999 | Shackleton et al. ......... 382/195 |

FOREIGN PATENT DOCUMENTS

| | | |
|---|---|---|
| GB | 1286316 | 8/1972 |
| GB | 2016276 | 9/1979 |

* cited by examiner

*Primary Examiner*—Mark Bockelman
(74) *Attorney, Agent, or Firm*—Harold James; Robert L. Epstein; James & Franklin, LLP

(57) ABSTRACT

An artificial system for vision and the like in which a camera views an object and creates signals corresponding thereto which are conveyed to the nervous system of the subject and produce corresponding sensations such as phosphenes in the subject's nervous system, in which the effectiveness of the system in conveying intelligence to the subject is enhanced by converting light-corresponding and dark-corresponding portions of the camera-produced signals into dark-corresponding and light-corresponding portions of the actual sensation-producing signals. Other enhancements include producing a comparatively bright signal of the edge of the object being viewed, the signals applied by a multiplexer which applies the plurality of pulses sequentially to particular locations. Other aspects include providing the subject with a rangefinder which causes sensations that periodically vary, as in brightness, at a rate corresponding to the distance to the object being viewed as well as providing an adjustable signal amplifier to produce a controllable "zoom" effect.

6 Claims, 4 Drawing Sheets

ARTIFICIAL SYSTEM FOR VISION AND THE LIKE

BACKGROUND OF THE INVENTION

The present invention relates to improvements in artificial systems for vision and the like which produce sensations such as phosphenes in the subjects. (The term "subject" is here used to refer to an individual, such as a totally or partially blind individual, using the system in question.)

It has long been known that a blind individual can be made to perceive a truly visual sensation when stimulations such as brief pulses are applied to electrodes implanted in contact with the nervous system of the subject. A pulse or train of pulses directed to a given electrode connected to a unique location results in the stimulated perception by the subject of a spot or cluster of light, called a phosphene, at its own particular location. A relatively small number of phosphenes created by stimulation of electrodes appropriately selected from an implanted array will present to the subject a pattern of light corresponding to that which, at any given instant, a camera aimed by the subject, as by being attached to his head, "sees". (The term "camera" is here used in its broadest sense to denote a device which senses ["sees"] a particular object or series of objects and produces a corresponding set of signals.)

Those signals are, in a known artificial vision system, conveyed through the subject's skull to a series of individual electrodes in contact with predetermined spots at appropriate locations of the subject's brain cortex, whether the visual cortex or the association cortex, each such electrode, when appropriately energized by a received signal, producing a uniquely located phosphene sensed by the subject. The selection of individual electrodes to be signal-energized at any particular moment defines the stimulated image corresponding to what the camera senses. The subject, aware of the phosphenes existing at any given moment, thus "sees" something which to him represents a particular object or shape.

Recently significant improvements have been made in such systems, especially but not exclusively artificial vision systems, giving to the subject an increasingly effective "sight", and providing to the supervisor of such systems and the designer of improvements therein a greater facility in understanding what the subject actually "sees" and to what extent that corresponds to actuality, so that potential improvements can more expeditiously be carried out and evaluated.

SUMMARY OF THE INVENTION

To create in the subject's brain a set of sensations which represent a particular object or shape has presented a problem. To do so with equipment which can be conveniently carried about by the subject greatly complicates the problem. This patent relates to recent improvements in systems of this type which materially expand their usability and practicability. Those improvements fall into two closely related categories—matters directly affecting what the subject "sees", and matters improving the ability of the designer-supervisor of the system to ascertain and evaluate how the system is actually functioning so as to guide him in making further improvements.

To these ends it has been found that the intelligibility and meaningfulness to the subject of the phosphene-produced image is significantly enhanced when (a) that image is caused to be a negative rather than a positive of what the camera senses—in other words, the dark and light portions of the camera-sensed object are reversed into light and dark signal portions respectively—and (b) the edges of the viewed object are brightly outlined.

A meaningful image can be produced in the nervous system of a subject using only a limited number of available electrodes, thus reducing the signal-producing and -manipulating requirement of the system. Moreover, it has been found that the effectiveness of such an image can advantageously be improved by applying, for a given camera signal, a series of similar pulses to each operative electrode. Through the use of a multiplexing circuit a given pulse is applied sequentially to each of a series of selected electrodes, that pulse is then reapplied sequentially to that series of electrodes, and so on, so that a given camera signal is effectively utilized to energize a group of selected electrodes with sequential pulses.

Primarily because of weight and size considerations, the camera used in a system of the type under discussion must be extremely simple. For example, in the artificial vision system presently in use the camera is a miniaturized TV camera carried by, and contained within, a single lens area of what appears to be an ordinary pair of sunglasses. Optically such a camera is not very versatile and in particular cannot optically magnify or modify that which it senses. However, I have found that if approximate circuitry is provided between the camera and the electrodes on the subject's nervous system which will controllably magnify the amplitude of the signal produced thereby, that will in effect magnify the perceived object and thus produce a "zoom" effect upon the phosphene image, the area of which is fixed. That amplification variation can be under the control of the subject, who can then produce the "zoom" effect whenever and to whatever extent desired.

One problem with phosphene-produced images is that they appear to be at no particular distance from the subject but instead to more or less float in space, whether the object they represent is close to or at a distance from the subject. This clearly limits the effectiveness of the image in advising the subject accurately with respect to the object viewed. Rangefinders with variable audible output are known and could be used by blind subjects but they have the disadvantage of interfering with the subject's normal hearing or other senses. That disadvantage is avoided, in accordance with the present invention, by causing the distance sensed by the rangefinder to produce in the nervous system a visible distance indication—illumination of specific phosphenes to represent specific distances (e.g., near, medium or far) or periodic variations in the produced stimulation, for example, a variation in intensity in visible stimulation, and preferably a blinking on and off, at a rate corresponding to the sensed distance, thereby conveying distance-intelligence to the subject while at the same time not significantly interfering with the visual representation then being conveyed to him of the object being viewed nor with his normal auditory activities.

In particular the data processing carried out by the system in question takes the signal produced by the camera, feeds it through a link to a sub-notebook computer, obtains a corresponding output from the sub-notebook computer and feeds that output to a micro-controller, the corresponding output of the micro-controller being amplified before being applied selectively to the electrodes in the subject's nervous system.

There are several ways in which the supervisor-designer of the system may be kept aware in detail of the manner in which that system is operating in order for that individual to be able to conceive of and implement improvements. To that end, in the system of the present invention the camera is provided with means for indicating to the supervisor-designer where the camera is pointed at any given point in time. That pointer may conveniently comprise a small laser source attached to the subject's sunglasses which produces a visible narrow light beam which will impinge upon the object being viewed by the subject. Further to the same end, the supervisor-designer is provided with a dual display system which simultaneously exhibits for purposes of comparison what the camera actually sees and the corresponding configuration of the stimulations produced in the subject's brain.

Essential to such an evaluation in a particular artificial vision system is an accurate map setting forth, as precisely as possible, the location of each phosphene or group of phosphenes in the subject's "sight" corresponding to a given electrode. Phosphene maps have been made in the past by energizing a particular electrode and asking the subject to state or indicate where the phosphene thus produced is located. This is not as easy as it sounds because phosphenes as a group sometimes move about in the subject's visual field and because objective statements from the subject as to where a particular phosphene is located are often vague and sometimes misleading. According to the present invention a more accurate phosphene map, not as subject to such vagaries, is obtained by first energizing two selected electrodes to produce two separated reference phosphenes to define a reference line, such as a vertical line, then individually energizing additional electrodes each producing its own associated phosphene, and obtaining from the subject an estimate of the position of that additional phosphene relative to the two originally selected referenced phosphenes and to the reference line which the latter define.

Each of these improvements enables and enhances the functioning of a system such as an artificial vision system effective to promote individual mobility. The cumulative effect of these improvements gives rise to a significant step forward in such artificial sensing systems.

DESCRIPTION OF THE PREFERRED EMBODIMENTS

While many of the improvements here disclosed and claimed are applicable to several different types of artificial sensing systems, they are here specifically described as embodied in the at present preferred embodiment, a particular artificial vision system.

Figure 1:
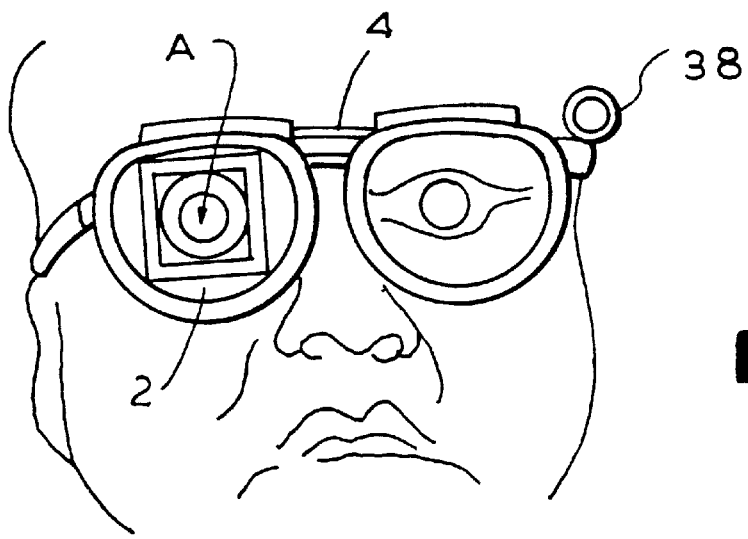
FIG. 1 is a pictorial view of the head of a subject utilizing an artificial vision system including the improvements of the present invention and showing the camera and the laser pointer mounted on sunglasses worn by the subject.
Figure 2:
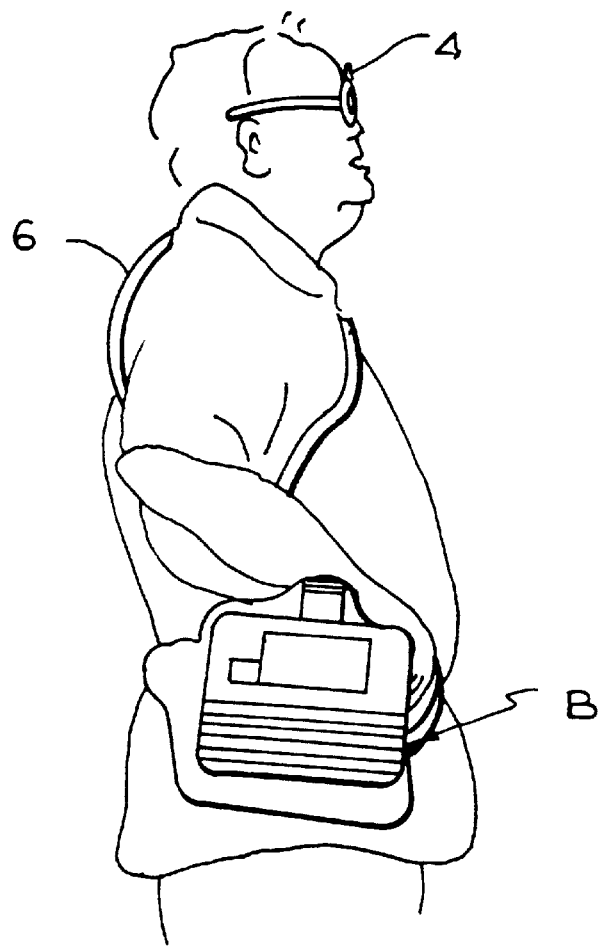
FIG. 2 is a side pictorial view of a subject showing the computer and electronics package which the subject carries.

As may best be seen in FIGS. 1 and 2, the subject is provided with a camera generally designated A which, for convenience, is mounted on the right lens 2 of a pair of sunglasses 4 worn by the subject. That camera is electrically connected to a computer and electronics package generally designated B carried by the subject, that package having an output cable 6 which is connected through the subject's scalp to an array of electrodes generally designated C and shown in FIG. 4 implanted on the subject's brain, either on the visual cortex or the association cortex. The associated circuitry and particularly the associated software, converts what the camera A "sees" into electric signals applied to selected electrodes of the array C, thereby to produce in the subject's consciousness a series of phosphenes. The location of the phosphene or phosphenes associated with a particular electrode does not correspond to the location of that electrode on the array C, and hence it is necessary to ascertain, for each such electrode, where the associated phosphene or phosphenes as sensed by the subject are located. This must be done in order to direct the signals produced by the camera A to the appropriate electrodes so as to produce for the subject a group of phosphenes representing what the camera "sees". FIG. 5 represents a typical map in visual space showing the location, for one subject, of the phosphenes associated with certain selected electrodes identified by corresponding number in FIG. 4.

When stimulated, each electrode produces perhaps 1–4 closely spaced phosphenes. Each phosphene in a cluster ranges in size up to the diameter of a pencil at arms length. Neighboring phosphenes in each cluster are generally too close to the adjacent phosphenes for another phosphene to be located between them.

The electrical connection between the electrodes of the array C and the appropriate locations on the brain of the subject is preferably accomplished through the use of a platinum foil ground plane perforated with a hexagonal array of 5 mm. diameter holes on 3 mm. centers. Flat platinum electrodes 1 mm, in diameter are centered in each hole. This ground plane confines all current to a location beneath the dura, thus eliminating discomfort due to dural excitation when stimulating some single electrodes and when other arrays of electrodes are stimulated simultaneously. The ground plane also eliminates most phosphene interaction when multiple electrodes are stimulated simultaneously, and provides an additional means of electrical safety that is not possible when stimulating between cortical electrodes and a ground plane outside the skull. Each electrode is connected by a separate teflon insulated wire to a connector contained in a percutaneous pedestal accessible at the interior of the subject's scalp.

Figure 3:
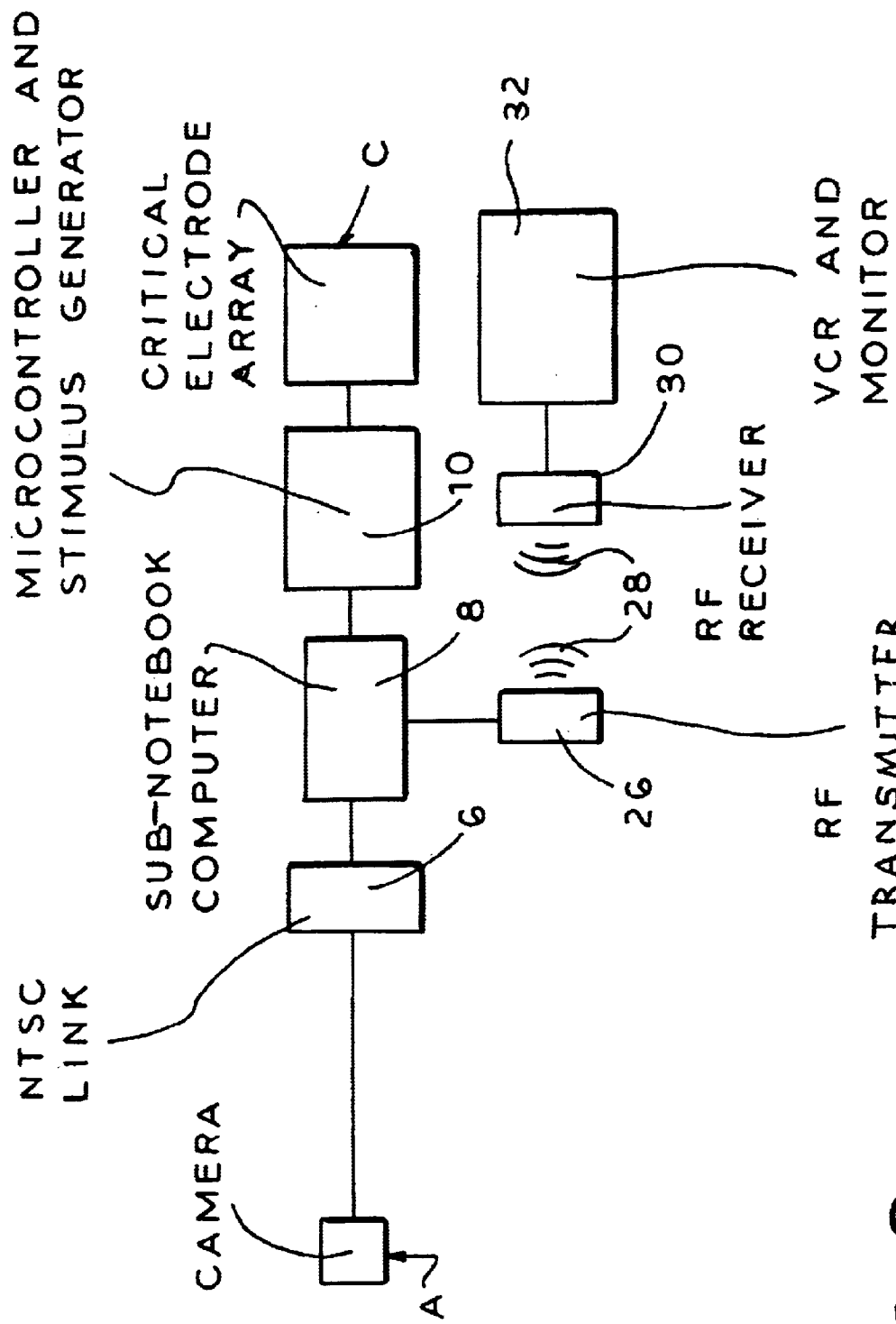
FIG. 3 is a block diagram of a typical system.

As shown in FIG. 3, the signals produced by the camera A—normal conventional television signals—are fed to link 6, such as the known National Television Standard Committee ("NTSC") link, which converts the normal television signal to a digital video signal that a computer can "understand". The output of that link 6 is fed to a sub-notebook computer 8, which in turn feeds a micro-controller and stimulus generator 10, which in turn produces the signals to select and stimulate the appropriate electrodes of the implanted array C.

In a preferred embodiment the camera A is a 492×512 pixel CCD (Charge-Coupled-Device") black and white television camera powered by a 9 volt battery. This f 14.5 camera has a 69° field of vision and utilizes a pinhole aperture instead of a lens to minimize size and weight. It also incorporates an electronic "iris" for automatic exposure control.

The sub-notebook computer 8 incorporates a 233 MHz microprocessor with 32 MB of RAM and a 4.0 GB hard drive. It also has an LCD screen and keyboard. It was selected because of its very small size and light weight. The belt pack B contains the link 6, the sub-notebook computer 8, the micro-controller 10 and associated circuitry and software. The computer and electronics package together are about the size of a dictionary and weigh approximately 10 pounds, including camera, cables, and rechargeable batteries. The battery pack for the computer will operate for approximately 3 hours and the battery pack for the other elements will operate for approximately 6 hours.

Stimulation delivered to each electrode typically consists of a train of six pulses delivered at 30 Hz to produce each frame of the image. Frames have been produced with 1–50 pulses, and frame rates have been varied from 1 to 20 frames per second. Frame rates of 4 per second currently seem best, even with trains containing only a single pulse. Each pulse is symmetric, biphasic (−/+), with a pulse width of 500 usec per phase (1,000 usec total). Threshold amplitudes may vary +/−20% from day to day; they are higher than the thresholds of similar electrodes without the ground plane, presumably because current shunts across the surface of the piarachnoid and encapsulating membrane. The system is calibrated each morning by re-computing the thresholds for each electrode, a simple procedure that takes the volunteer approximately 15 minutes with a numeric keypad.

Figure 4:
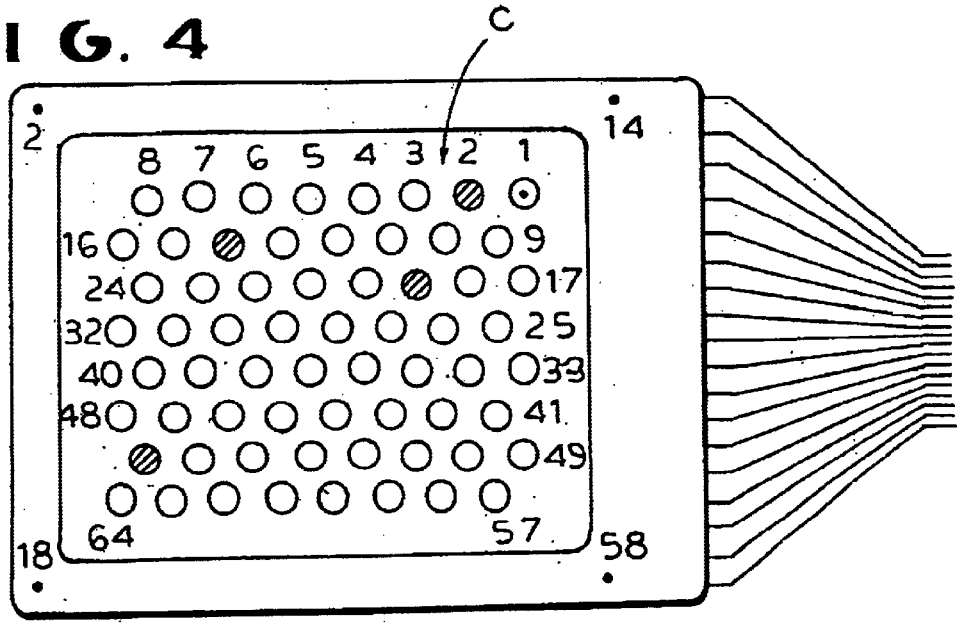
FIG. 4 is an enlarged planar view of the electrode layout as applied to the surface of the subject's brain.
Figure 5:
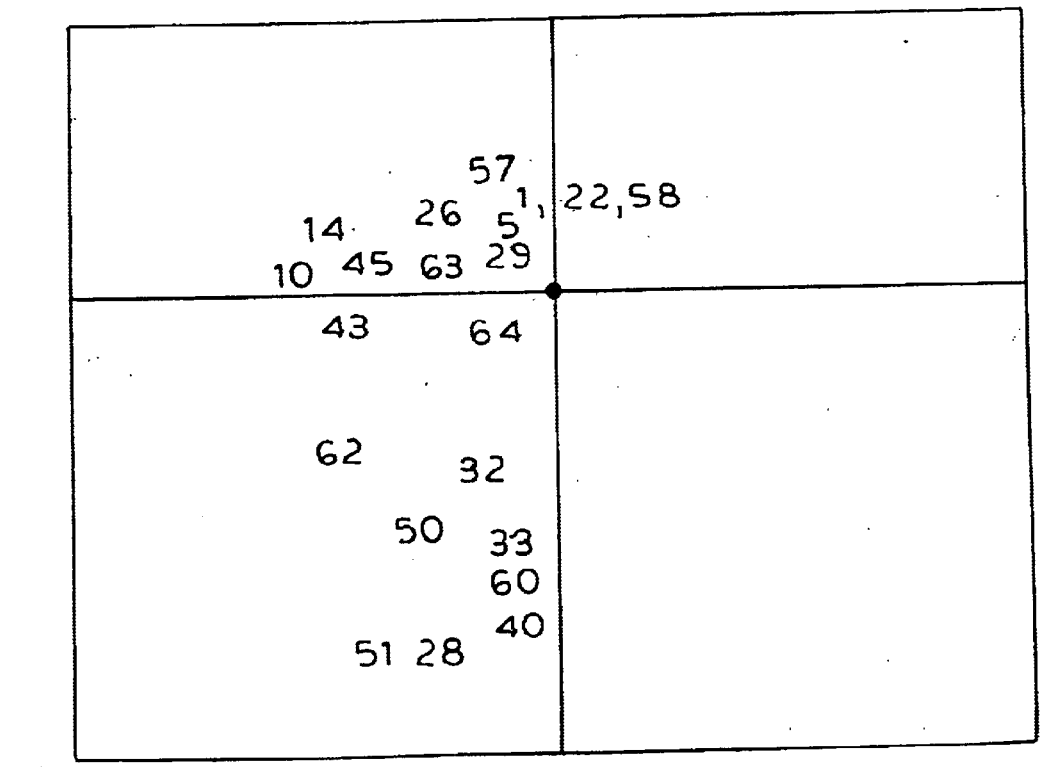
FIG. 5 is a typical map in visual space of some of the phosphenes produced by particular electrodes of the array of FIG. 4.

In order to extract intelligence from the camera segment it is not necessary to use all of the 64 electrodes that are provided in the installation illustrated in FIG. 4, but as a practical matter a plurality of such electrodes must be simultaneously energized if a meaningful phosphene image is to be produced. It has been found that as few as 10 electrodes need be energized to produce a particular frame. With an appropriate pulse width and pulse frequency it is possible to energize the desired number of electrodes from a single drive by utilizing the time slots between the pulses destined for one electrode to receive pulses selected for a series of other electrodes. This is readily accomplished by using a conventional demultiplexer circuit in reverse. The conventional demultiplexer circuit accepts a series of inputs and feeds them in predetermined order to a single output. As used here, the demultiplexer circuit will take a single input signal and feed it seriatim to a number of outputs corresponding to the desired number of electrodes to be energized. Thus the multiplexer circuit will feed a first pulse to a series of electrodes in order, it will then feed a second pulse to the same series of electrodes preferably in the same order, and so on. The frequency at which the pulses are produced and the width of those pulses determine the intervals of time available for pulses to be directed to a selected series of electrodes.

Brightness of the phosphenes can easily be modulated by changes in pulse amplitude. However, provision of "gray scale" has not proven very valuable so far, probably because of the combination of tunnel vision and limited resolution.

The phosphene display is planar, but is of uncertain distance, like the stars in the sky. This presents to the subject a problem in depth perception. It is normally difficult for him to determine whether one sensed object is at the same distance from the camera as another sensed object. Ultrasonic rangefinders have been known for many years and have been used by the blind. Conventionally such rangefinders translate sensed distance into normally sensed signals such as audio signals, but those normally sensed signals interfere with the ability of the subject to use his sense of hearing or other sense in its normal fashion. In accordance with the present invention, to overcome that disadvantage an ultrasonic rangefinder may be utilized with the present system, as, for example, being secured to the left lens 10 of the sunglasses 4, but the output of that rangefinder is caused to give rise in the nervous system to a visible distance indication—illumination of specific phosphenes to represent specific distances (e.g., near, medium, or far) or periodic variations in the produced stimulation, for example a periodic variation in brightness, and preferably a blinking on and off, at a rate corresponding to the sensed distance. Thus the acuity and intelligibility of the subject's sense of hearing is not compromised although the subject is given an indication of the relative distance to various objects.

The camera A must be small, light and inconspicuous if it is to be carried by the sunglasses 4. Such a camera is necessarily optically simple. For example, the camera 2 disclosed in FIG. 1 has a non-variable 69° field of vision and any attempt to alter its field of vision or to provide a "zoom" feature would involve heavy and conspicuous equipment, which is of course contraindicated. However, if the system between the camera A and the electrode array C is provided with appropriate circuitry to controllably magnify the amplitude of the stimulation, magnification of the signals fourfold or more will produce an image which, because the field of vision is limited, exceeds the tunnel limitation of the camera, thus producing a "zoom" effect. The amplification can be under the control of the subject if desired.

Figure 6:
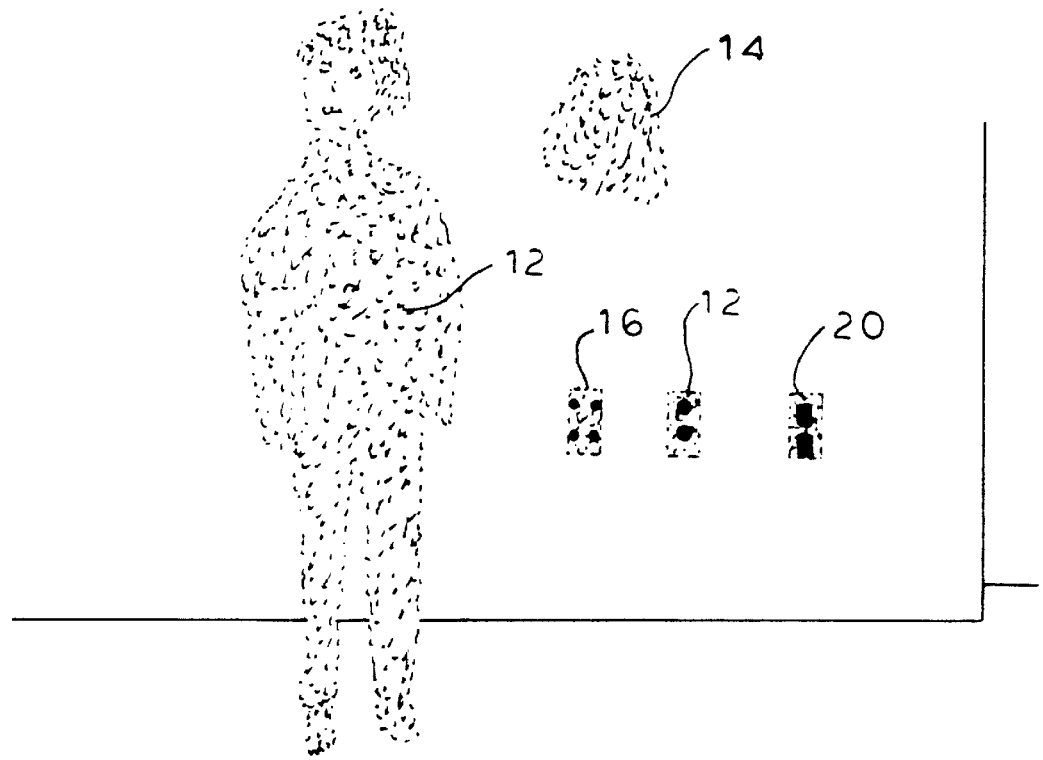
FIG. 6 is a photographic view of a particular test scene to be viewed by a subject.
Figure 7:
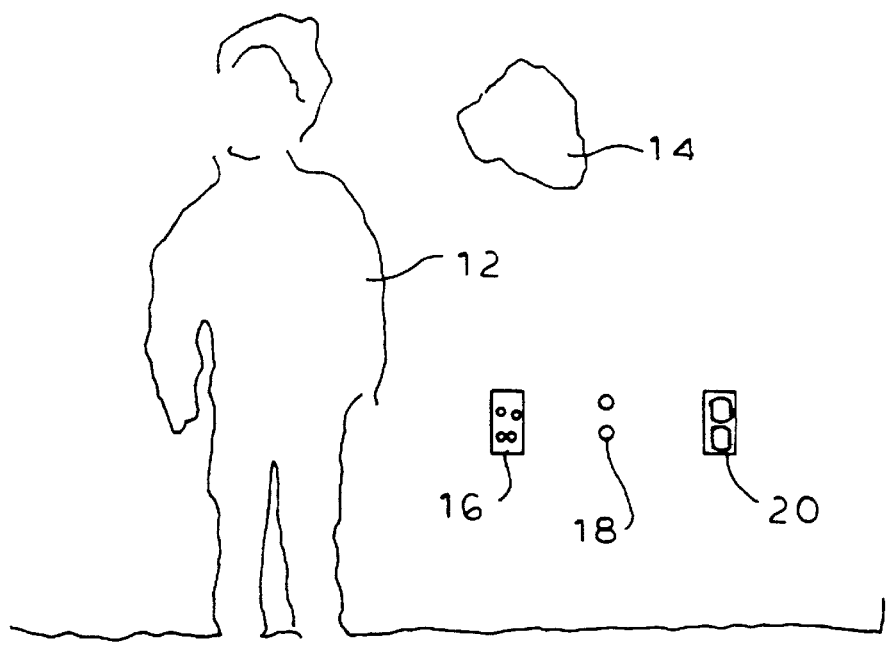
FIG. 7 is a representation of what the subject preferably "sees" when he views the test scene of FIG. 6.

One limitation on the intelligibility of phosphene images in the subject's brain is the number of frames that can be sequentially created in a given period of time. The greater the number of frames in a period of time the more intelligence is transmitted to the subject, but the greater are the demands which are placed on the system, and the system is essentially limited by the state-of-the-art and the necessity that it be readily portable by the subject. Producing one frame per second is too slow to provide good mobility to the subject, and merely increasing the frame rate, all else being constant, does not itself produce an phosphene image of appropriate clarity. These problems have been greatly amelio-rated by two steps—darkness inversion and edge detection. Darkness inversion means that the signal from the camera A is in effect reversed or inverted, so that dark-sensed portions of the camera-viewed image result in light-producing signals applied to the electrodes and light-sensed portions of the camera-viewed image result in dark-producing signals applied to the electrodes. Edge detection—producing an image in which edges are sensed and intensified—is a known procedure in other contexts. When edge detection, particularly using Sobel filters, is employed in a system of the type under discussion, and particularly when it is used in conjunction with darkness inversion, that permits processing and transmitting images in a 233 MHz system at a speed up to 8 frames per second with existing equipment, which in turn results in greatly improved transmission of intelligence to the subject. FIGS. 6 and 7 are illustrative of the effects thus achieved. Fig. 6 discloses a typical demonstration set up comprising a mannequin 12, a cap 14, and three different sockets 16, 18, and 20 mounted on a wall 22. With darkness inversion and particularly with edge detection the resultant phosphene image is as shown in FIG. 7. Sensing an image of the type disclosed in FIG. 7 the subject is easily able to find the mannequin and the cap and to detect the sockets. Similarly, doorways would appear as an outline of white phosphenes on a black background, making the location of the doorway very clear to the subject.

Important to the operation and particularly the improvement of the system is the ability of the supervisor or designer of the system to know precisely how the system is operating, what it is accomplishing and what it is not accomplishing. the system of the present invention is provided with several new features to improve supervision and facilitate improvement of design.

For example, it is important that the supervisor-designer (hereinafter generically designated "operator") know what particular phosphene pattern or other stimulation is being presented to the subject at any given moment. To that end, and as shown in FIG. 3, the sub-notebook computer 8 may not only send intelligence to the micro-controller 10 but also send it to an RF transmitter 26 which is electromagnetically linked at 28 with RF receiver 30 which in turn is linked to a VCR and monitor 32. Hence the monitor 32 lets the operator know what the subject is "seeing". Simultaneously a display may show to the operator what the camera A is seeing. In its preferred form the two displays—what the camera sees and the corresponding phosphene map—may be provided on a split screen for convenient comparison.

Along the same lines, it is helpful to the operator, as he observes the subject using the system, to know precisely in what direction the subject is "looking" at any given moment, that information to be correlated with the displays just described, observation of the physical movements of the subject, or otherwise. To that end, and as may be seen in FIG. 1, the sunglasses 4 worn by the subject carry on a temple piece a laser generator 38 which emits a narrow beam of light directed in the same direction as that in which the subject is looking and which therefore will produce a visible spot of light at the appropriate point on the scene being viewed.

The phosphene map is produced by selectively energizing particular electrodes and asking the subject to identify the location of the phosphene as he sees it. This procedure is complicated by the fact that all phosphenes are produced in a relatively small area, which makes pointing difficult, and that difficulty is compounded by the fact that phosphenes move with movement of the subject's eye. Accuracy of the phosphene map for each subject is important in selecting the particular electrodes to be energized at any given moment in order to produce in the subject's brain an accurate image of what the camera is "seeing". In order to produce a more accurate phosphene map a new procedure has been created—first two pre-selected electrodes are energized to produce two spaced phosphenes which define a reference line, generally but not necessarily vertical. Then while those two phosphenes continue to be produced, other individual electrodes are individually energized and the subject is asked to identify the location of the phosphene thus produced relative to the locations of the two original phosphenes and the reference line which the latter define. This is usually done in terms of the vertical spacing between each individually produced phosphene and the two reference phosphenes as well as the distance of the individually produced phosphene to one side or the other of the reference line connecting the original phosphenes. In this way, a more accurate phosphene map is produced.

With a system of the type here disclosed a blind subject is readily able to navigate among a "family" of three mannequins—standing adult male, seated adult female and standing 3-year old child—randomly placed in a large room, without bumping into any of them. He can then retrieve a cap which has been placed on a wall in a random location, and can place that cap on the head of a designated mannequin. Subjects are able to recognize and identify characters in various standardized forms used in acuity tests, such as Snellen letters, Landolt links and Lea figures displayed to the subjects as pure black figures on a pure white background of a size corresponding to a visual acuity of approximately 20/2400.

The conversion of camera signals or other signals into appropriate electrode pulses is accomplished by means of circuity and particularly software which is state-of-the-art.

The artificial vision system in its present stage of development has not yet been perfected to the degree that it will permit the subject to read easily, but it does give the subject sufficient intelligence so that he can move about safely and perform various physical tasks. By way of example, a subject provided with a system of the type here described has not only been able to move about an apartment but has even been able to enter a subway station and determine the location of the doors on a train that has pulled into the station.

While a limited number of embodiments of the present invention have been here specifically disclosed, which can function individually or cumulatively, and many of which are not limited to use in an artificial vision system, it will be apparent that many variations may be made therein, all without departing from the spirit of the invention as defined in the following claims.

I claim:

1. An artificial vision system comprising means for creating electrical signals corresponding to a visual image of an object, an implantable brain stimulator for producing phosphenes in the brain of a visually impaired individual, and an electrical connection between said signal creating means and said stimulator which comprises signal modifying means effective to produce said phosphenes corresponding to a modified image of said object which modified image has a comparatively bright object outline when compared to the remaining portion of said modified image.

2. The artificial vision system of claim 1, in which said signals correspond to light and dark portions respectively of said object and in which said signal modifying means is effective to cause the electrically created signals corresponding to light and dark portions of said object to be modified so as to produce phosphenes having dark and light portions in said modified image of said object respectively.

3. An artificial vision system comprising means for creating electrical signals corresponding to light and dark portions of a visual image of an object, an implantable brain stimulator for producing phosphenes in the brain of a visually impaired individual, and an electrical connection between said signal creating means and said stimulator which comprises signal modifying means effective to cause the created electrical signals corresponding to light and dark portions of said object to be modified so as to produce phosphenes corresponding to the dark and light portions of said object respectively.

4. An artificial vision system comprising means for creating electrical signals corresponding to a visual image of an object, an implantable brain stimulator for producing phosphenes in the brain of a visually impaired individual, and an electrical connection between said signal-creating means and said stimulator, said system further comprising a rangefinder having an output reflecting the distance from said individual to said object, said output appropriately modifying said phosphene-producing signals in accordance with said distance to indicate object distances to the user.

5. The artificial vision system of claim 4, in which said modification of said phosphene-producing signals comprises essentially varying the amplitude of those signals at a rate corresponding to said distance.

6. An artificial vision system comprising means for creating electrical signals corresponding to a visual image of an object, an implantable brain stimulator for producing phosphenes to the brain of a visually impaired individual, and an electrical connection between said signal creating means and said stimulator which comprises a variable signal amplifier active on said signals and under the control of the individual, thereby to controllably vary the degree of signal amplification and produce phosphenes creating a "zoom" effect.

* * * * *